United States Patent [19]

Doerr

[11] Patent Number: 4,900,148
[45] Date of Patent: Feb. 13, 1990

[54] APPARATUS AND PROCESS FOR MEASURING AN OPTICAL CHARACTERISTIC OF A PREDETERMINED PORTION OF A FLAT OBJECT

[75] Inventor: Stephen Doerr, Closter, N.J.

[73] Assignee: Nabisco Brands, Inc., Parsippany, N.J.

[21] Appl. No.: 806,784

[22] Filed: Dec. 9, 1985

[51] Int. Cl.⁴ .............................................. G01N 21/01
[52] U.S. Cl. ..................................... 356/244; 356/432
[58] Field of Search .............. 356/244, 246, 445, 444, 356/432, 434, 440, 443; 250/559

[56] References Cited

U.S. PATENT DOCUMENTS

| | | | |
|---|---|---|---|
| 2,847,859 | 8/1958 | Lynott | 74/37 |
| 2,891,314 | 6/1959 | Haschek | 33/1 |
| 2,981,123 | 4/1961 | McHugh | 74/665 |
| 3,184,600 | 5/1963 | Potter | 250/237 |
| 3,241,243 | 3/1966 | Speer | 33/174 |
| 3,345,747 | 10/1967 | Sattler | 33/1 |
| 3,491,716 | 1/1970 | Ranford | 116/129 |
| 3,495,519 | 2/1970 | Alfsen et al. | 95/36 |
| 3,568,321 | 3/1971 | Map et al. | 33/18 |
| 3,620,627 | 11/1971 | Davies | 356/244 |
| 3,665,610 | 5/1972 | Schlau et al. | 33/18 R |
| 3,760,505 | 9/1973 | Clark | 33/18 R |
| 3,950,853 | 4/1976 | Andrew | 33/79 R |
| 4,176,455 | 12/1979 | Copeland et al. | 33/1 M |
| 4,237,616 | 12/1980 | Tobias | 33/286 |
| 4,397,560 | 8/1983 | Andresen | 356/440 |
| 4,596,468 | 6/1986 | Simeth | 356/444 |

Primary Examiner—Vincent P. McGraw
Assistant Examiner—S. A. Turner
Attorney, Agent, or Firm—Richard Kornutik

[57] ABSTRACT

An apparatus for measuring an optical characteristic, such as color, of an object having two edges comprises a support for the object, a stop member slideable but releasably secureable to the support in a variety of different positions allowing for variation of the position of the stop member in two dimensions, and an optical instrument for measuring the desired optical characteristic. In use, the two edges of the object to be tested are abutted against two stop surfaces on the stop member and the optical instrument lowered adjacent the object to determine the optical characteristic of a portion of the object beneath the instrument. A number of similar objects can be tested by abutting them in turn against the stop surfaces of the stop member.

17 Claims, 3 Drawing Sheets

APPARATUS AND PROCESS FOR MEASURING AN OPTICAL CHARACTERISTIC OF A PREDETERMINED PORTION OF A FLAT OBJECT

BACKGROUND OF THE INVENTION

This invention relates to an apparatus and process for measuring an optical characteristic. More specifically, this invention relates to an apparatus and process which allows rapid and easy placement of a series of similar articles in the same position below a meter for measuring the desired optical characteristic.

Food products and other consumer items are conventionally packed in printed wrappers in order that the products will make an attractive display on a supermarket shelf, or other retail display, thereby enhancing their attractiveness to their consumers. In order to achieve such attractiveness to consumers, the wrappers are frequently printed in several colors and may bear complex designs. For example, a wrapper intended for a cookie package may be color-printed with a picture of the cookies contained therein, while a wrapper intended for breakfast cereal may be decorated with a picture of the breakfast cereal in a bowl with milk and pieces of fruit.

The high-speed packaging machines used to pack mass-produced food and other consumer items may use hundreds of such wrappers per hour, and thus the wrappers are printed in very large batches with perhaps tens of thousands of individual wrappers in each batch. It is well known to those skilled in the art of printing such wrappers that, in the long printing runs required for multi-color printing of such large batches of wrappers, it is in practice impossible to keep the colors abolutely constant throughout the long printing run. Consequently, in order that the producers of food and other consumer items can produce a consistent product, such producers must constantly check the quality of the color printing on the wrappers they use and discard wrappers which differ too greatly from the desired colors.

Hitherto, decisions regarding the acceptability of the colors on wrappers have been made visually by personnel operating the packaging lines. The personnel are provided with samples showing the correct color and the limits of acceptable variation and simply compare the packages visually with these standards. Such subjective color comparisons have serious disadvantages. Subjective human color judgements are notoriously variable, especially when made by personnel who have little training and/or experience in color comparisons. Furthermore, the lighting in factories is often far from ideal for making such color comparisons, and an individual who is called to make such color comparisons throughout (say) an eight-hour shift will rapidly become fatigued. In addition, there are of course variations introduced by the physical and mental state of the individual, and futher inaccuracies introduced by the fact that packaging machines are frequently run 24 hours a day so that several different persons will be responsible for making the color comparisons on various shifts.

Instruments have now been developed which can measure a precise absolute value of specific colors, and store and process such information. These instruments provide an objective analysis of color quality in color-printed materials which is much less susceptible to variation than the subjective comparisons hitherto employed. Unfortunately, it is difficult to apply such instruments to control of color under the practical conditions in a packaging plant. Unlike the human eye, which can look at an entire wrapper having several different colors arranged in a large number of discrete areas in a design and make a succession of color comparisons of the individual colors with a set of standards lying adjacent the wrapper, the instruments must be brought closely adjacent a constant point on the succession of wrappers to be color tested. Not only may some of the color areas to be tested be small (as for example where a package is printed with a picture of cereal having pieces of fruit dispersed therein, and it is desired to carry out a color measurement on the pieces of fruit), but even where large areas of color are involved it is not sufficient merely to bring the instrument adjacent a large area of background color since it common practice to vary the intensity of a color within a large area covered by that color. Accordingly, it is not possible to rely upon an operator simply placing a measuring instrument manually adjacent a portion of the wrapper on which it is desired to measure the color, since invariably as the operator makes repeated measurements the position at which the instrument is placed adjacent the wrapper will vary, thereby giving faulty readings. Thus, in order to obtain reliable readings from such an instrument it is necessary to devise some form of locating device which will locate the instrument adjacent the same predetermined point on a series of wrappers.

Numerous forms of mechanical locating device have been described in the prior art. For example, U.S. Pat. No. 3184600 to Potter describes an apparatus for measuring coordinates in two dimensions. In this apparatus a stylus and sensor assembly is mounted on the end of a drafting table type arm so that it can move above a flat plate without rotation. A translucent plate is disposed above the stylus and sensor assembly parallel to the flat plane and is covered with grid lines. The stylus and sensor assembly comprises a stylus, two photocells and an upper plate. The upper plate has two separate halves, one of which is engraved with lines parallel to the X-axis of the lines on the translucent plate, while the other half of the plate is engraved with lines parallel to the Y-axis of the translucent plate. One photocell is placed below each half of the upper plate. As the two sets of lines on the upper plate move across the grid on the translucent plate, interference effects occur which enable the photocells in the stylus and sensor assembly to determine the X and Y coordinates of the stylus.

U.S. Pat No. 3950853 to Andrew describes an accessory for a track type drafting machine in which a drafting machine head comprising two rules disposed at right angles to one another is rotatably mounted on a carriage. This carriage is movable along a first track, which is itself moveable along a second track disposed at right angles to the first track. Consequently, by moving the drafting machine head along the first track, and the first track along the second track, the drafting head can be positioned at any position above a drawing board. Graduated tapes are provided on the tracks to enable the X and Y coordinates of the drafting head to be measured accurately.

U.S. Pat. No. 417645 to Copeland et al. describes a plotting apparatus in which a shaft is moveable along two slots extending perpendicular to the length of the shaft. A collar is slideable along the shaft so that by movement of the collar along the shaft, and of the shaft within the slots, the collar can move in two mutually perpendicular directions. A power-operated plotting arm including first and second arms is mounted on the collar. The power drive for the plotting arm pivots the first and second arms through controlled angles in response to the input of a pair of angular coordinate signals, thereby providing a high degree of resolution between points in the plotting operation.

Other prior art locating devices include apparatus for movement of a stylus or similar instrument in two dimensions by means of a pair of rigid rods disposed at right angles to one another. For example, U.S. Pat. No. 2847859 to Lynott describes such a positioning device. In the apparatus shown in FIG. 4 of this patent, four carriers are arranged to interact with an endless belt driven by a pulley. The four carriers are interconnected by two rods lying at right angles to one another and passing through sleeves also disposed at right angles to one another. This apparatus enables controlled positioning in an X-Y plane of a stylus or similar device attached to the two sleeves.

U.S. Pat. No. 2891314 to Haschek describes a map assembly including a location director which is mounted on two rods disposed at right angles to one another. Two pointers attached to the two rods indicate the X and Y coordinates of the location director on scales provided on two mutually perpendicular tracks disposed along two edges of the map. The patent suggests that a spotlight be provided on the location director to indicate a particular location on the map.

U.S. Pat. No. 2981123 to McHugh describes a coordinate positioner comprising a cutting block mounted on a first pair of smooth bearing shafts. A first threaded shaft is disposed between the first smooth shafts and extends through a threaded aperture in the cutting block, so that when the first threaded shaft is rotated the cutting block will slide in a precisely controlled manner along the smooth shafts. The ends of the two first smooth shafts and the first shaft are received in a pair of blocks, which are themselves slidable along a second pair of smooth shafts by means of a second threaded shaft.

U.S. Pat. No. 3241243 to Speer describes a hole center locating apparatus in which a contact sensing assembly can be translated in three dimensions. The apparatus disclosed in this patent operates in a manner generally similar to that in McHugh described above, but translates the contact sensing assembly in three dimensions using rack-and-pinion mechanisms, rather than the threaded shaft and collar mechanisms used in McHugh.

U.S. Pat. No. 3345747 to Sattler describes a mechanical coordinating device intended for use with machine tools. An apparatus shown in FIGS. 1–4 of this patent measures movement of a tool or other implement in a X-Y plane by causing photocells arranged to move with the implement to track across steel rules, thereby generating pulses when the photocells pass graduations cut into the rules. These impulses are electronically recorded as coordinates on appropriate digital counters.

U.S. Pat. No. 3495519 to Alfsen et al. describes an "XY table" which operates in a manner generally similar to the apparatus described in McHugh discussed above, except that the cutting block in McHugh is replaced with a plate supported upon a pair of spaced shafts. Like the apparatus shown in McHugh, the apparatus described in Alfsen effects movement of the plate in two perpendicular directions by means of threaded shafts passing through threaded collars.

U.S. Pat. No. 3665610 to Schlau et al. describes a plotter toy in which a pencil can moved in two dimensions across a sheet of paper by manual manipulation of a pair of knobs.

U.S. Pat. No. 3760505 to Clark describes a tracing device which is rather similar to the apparatus described in Haschek discussed above. In the Clark apparatus, a stylus is mounted upon a pair of rods disposed at right angles to one another, and these rods are moveable by means of a continuous loop of thread passing around pulleys.

U.S. Pat. No. 4397560 to Andresen describes an apparatus in which a magnetic locating device is used to locate a photocell at a plurality of positions on a rectangular grid. This apparatus is a photometer for sensing the optical density of a plurality of liquids located in a microtray provided with a rectilinear array of wells. The microtray is supported on a carrier having two hollow side members in which are enclosed elongate bar magnets disposed at right angles to one another. A light source is mounted on a cantilevered arm above the carrier, and a photocell is mounted on a support surface below the carrier. A light tube disposed below the light sources is provided with a detent which engages in the wells of the microtray. To enable the exact well being tested to be determined, two linear arrays of magnetic sensors are disposed beneath the support surface, these two linear arrays of sensors being disposed at right angles to one another. One of the sensors in each array is activated by the bar magnets, thereby enabling the exact well in the array of wells to be determined. Although the apparatus thus uses magnetic detection to detect which well is being tested, location of the wells is effected solely by the detent. Presumably, very accurate alignment of the wells is not necessary since the apparatus would normally be used for e.g. an ELISA assay, in which the whole area of any one well would be of the same color.

Other miscellaneous locating devices are described in the prior art. For example, U.S. Pat. No. 3491716 to Ranford describes a method for positioning a marker along two orthogonal axes which is somewhat similar to that in Haschek described above, except that instead of the marker being mounted on two rigid rods at right angles to one another it is moveable by means of a first cord extending along one axis. This cord is itself mounted by means of pulleys on a pair of shoes which slide along spaced tracks. Movement of the shoes along the tracks is controlled by means of a further pair of cords.

U.S. Pat. No. 3568321 to Maps et al. describes a plotting apparatus having a pin holding mechanism mounted for movement along an arm, which is itself moveable along opposed edges of a plotting surface.

Finally, U.S. Pat. No. 4237616 to Tobias describes a scanning path alignment apparatus including a pair of wires which are located one above the other in a plane that lies parallel or orthogonal to the center lines of a path which a scanning head is to view.

None of the prior art apparatus discussed above is very suitable for locating a color measuring instrument in a reproducible manner adjacent a predetermined point on a wrapper. Apparatus such as that described in McHugh, Speer, Sattler and Alfsen is bulky, complicated, and very expensive. Although such appratus is acceptable for use in costly numerically-controlled machine tools and similar devices, its bulk, complexity and cost renders it impractical for use in routine color determination of wrappers. The apparatus shown in Andresen is not capable of reproducibly locating a predetermined point with high precision. Most of the other prior art apparatus discussed above is intended for locating a point on a plane, or accurately measuring the location of such a point rather than merely reproducibly locating the same point on a series of sheets once that point has been located on the first sheet of the series. Consequently, such apparatus tends to be unnecessarily complicated and expensive for use in locating a measuring instrument adjacent a wrapper. Furthermore, in order to accommodate the need to place the instrument very closely adjacent the wrapper while effecting the color measurement, while still permitting rapid removal and replacement of wrappers, it is desirable that apparatus used in color measurement on wrappers allow for movement of the photocell toward and away from the plane of the wrapper. Most of the prior art apparatus described above does not permit movement of the stylus or other locating device perpendicular to the surface of the object on which the measurement is being effected. Finally, although an apparatus for effecting color measurements on wrappers only needs to locate an instrument at a single predetermined point for a given series of measurements, it must allow for variation in position in the predetermined point in two dimensions in order to accommodate variations in the printing of wrappers. This invention provides a simple, inexpensive apparatus which can meet all these requirements.

SUMMARY OF THE INVENTION

Accordingly, this invention provides an apparatus for measuring an optical characteristic of a portion of an object having a first edge and a second edge not parallel to the first edge, the apparatus comprising a support member having a substantially flat support surface, a stop member capable of lying adjacent the support surface and movable relative thereto along first and second non-parallel axes, this stop member being provided with first and second stop surfaces which are not parallel to one another, the first and second stop surfaces being arranged on the stop member such that, when the stop member lies adjacent the support surface, the first and second stop surfaces both extend in one direction away from the plane of the support surface, thereby enabling the object to rest upon the support surface with its first and second edges in contact with the first and second stop surfaces respectively, locking means for releasably securing the stop member in any one of at least first, second and third positions relative to the support surface, movement from the first position to the second position requiring a translation along the first axis and movement from the first position to the third position requiring a translation along the second axis, and metering means for measuring the optical characteristic of the portion of the object overlying a predetermined point on the support surface.

This invention also provides a process for measuring an optical characteristic of a portion of an object having a first edge and second edge not parallel to the first edge, the process comprising providing a support member having a substantially flat support surface, releasably securing, in a position fixed relative to the support surface, a stop member provided with first and second stop surfaces arranged on the stop member such that, when the stop member is secured relative to the support member, the first and second stop surfaces both extend in one direction away from the plane of the support member, placing the object on the support surface with its first and second edges in contact with the first and second stop surfaces respectively, placing a metering means for measuring the optical characteristic adjacent a predetermined point on the support surface, and measuring with the metering means the optical characteristic of the portion of the object overlying the predetermined point on the support surface.

DETAILED DESCRIPTION OF THE INVENTION

The optical characteristic measured by the apparatus and process of the present invention may be any one of the optical characteristics which is capable of being measured instrumentally, and accordingly the metering means used in the apparatus and process of the present invention may comprise any one or more of the instruments developed for measuring optical characteristics. The optical characteristics which can be measured by such instruments are well known to those skilled in the art of color measurement and include, for example, hue (the color itself, such as red, yellow, green, blue etc.), color value (the relative lightness/darkness of the color) and chroma (the vividness or dullness of the color). Commercially available instruments suitable for use in the present apparatus and process include the Hunter Lab D25-PC2 coloring meter, manufactured by Hunter Lab, 11495 Sunset Hills Road, Reston, Virginia 22090, the Macbeth 1500/PLUS color measurement system, sold by Macbeth, P.O. Box 950, Newburgh, New York 12550 and the Minolta Chroma Meter II, manufactured by Minolta Corporation and available from, inter alia, Lee Della-Croce Eastern Metro Associates Inc., Three Eva Lane, Planeview, New York 11803. For example, the Minolta Chroma Meter II can measure the chromaticity of an object using the parameters Yxy of the 1931 Commission International de L'Eclairage Standard, or the parameters L*a*b* of the 1976 CIE Standard. (In the 1931 Standard, Y is brightness and xy is tone, a combination of hue and saturation, while in the 1976 Standard L is color value, A is chroma and B is hue.)

The Minolta Chroma II and other instruments of this type can also be operated in a color deviation mode in which the parameters of a reference color sample stored in memory are compared with those of a sample placed before the meter. The use of such a color deviation mode may be useful in the process of the present invention since it allows one to use a sample of the ideal color of the wrapper, carton blank or other object being measured and thereafter to determine directly the deviation of successive samples from the standard. Some of such instruments are sold commercially with data processors which can not only display the individual color measurements read by the instrument but which can also store a series of such measurements and perform statistical calculations thereon. For example, the Minolta Chroma Meter II can be purchased complete with a Minolta Data Processor DP-100 for performing such display and statistical calculation functions. Such data processors may be incorporated in the apparatus of the present invention in order that, for example, when testing the ability of various printers to achieve the printing requirements of a particular job, one can compare a series of samples from the various printers in order to determine which provides the most consistent product.

Figure 1:
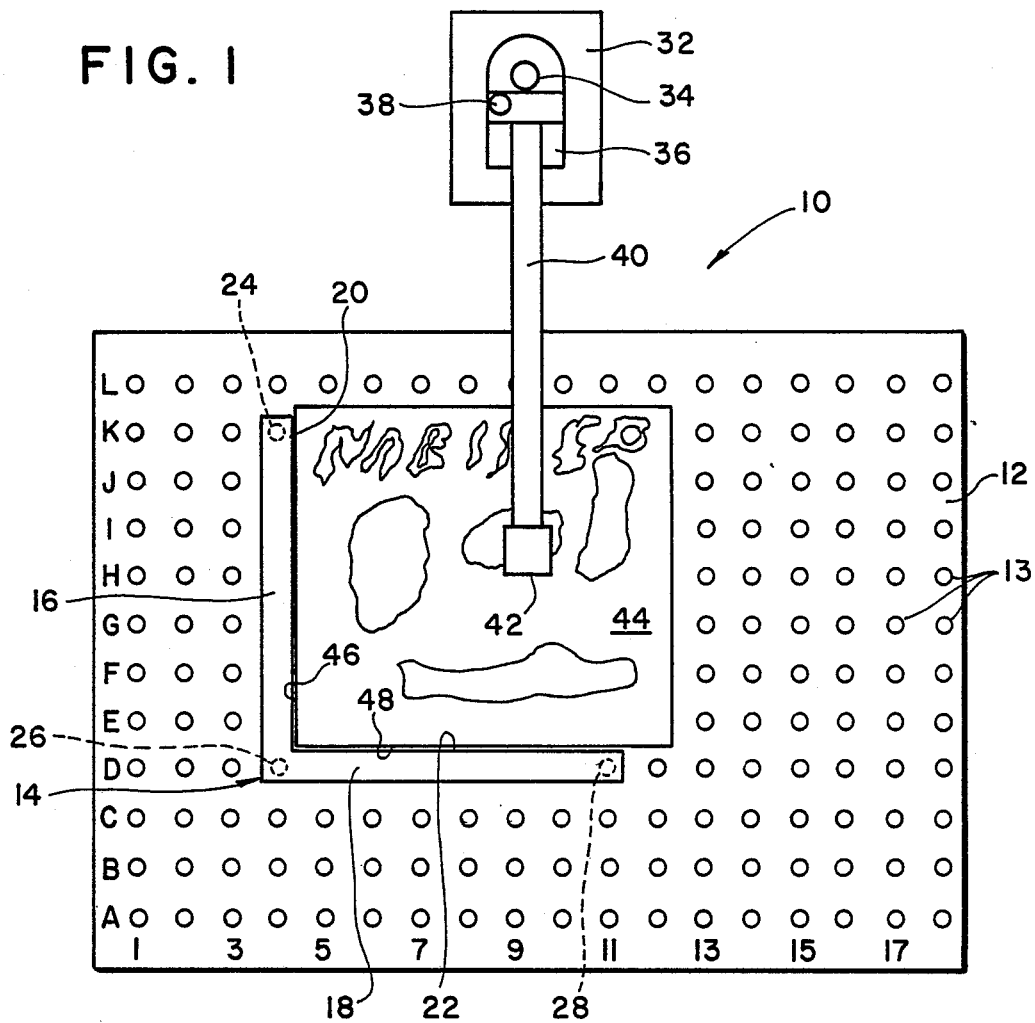
FIG. 1 is a top plan view of a first apparatus of the invention.
Figure 2:
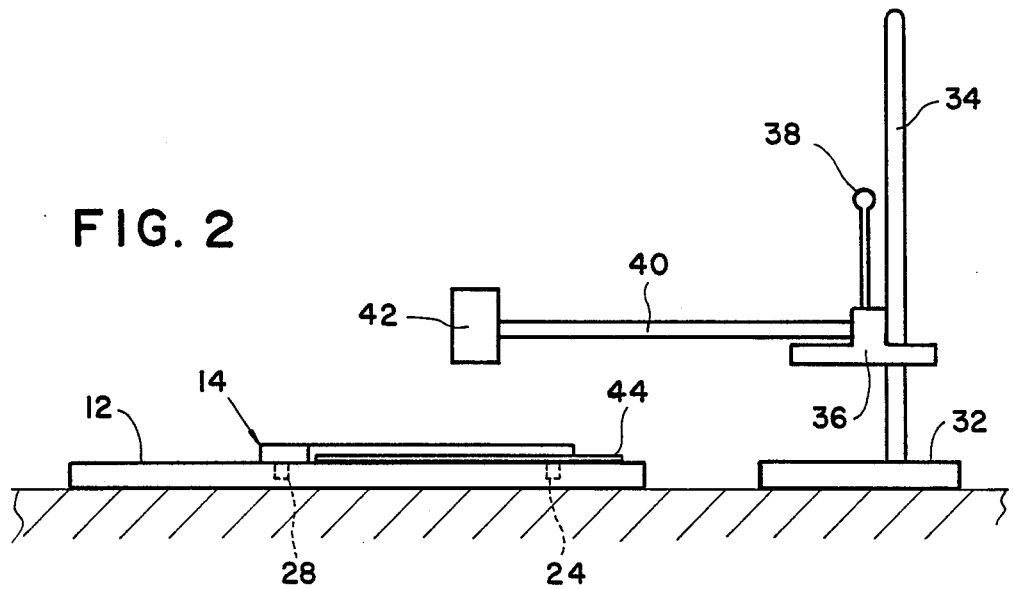
FIG. 2 is a side elevation of the apparatus shown in FIG. 1 looking in the direction of the arrow in that Figure.

The first apparatus of the invention, generally designated 10, shown in FIGS. 1 and 2 comprises a support member in the form a flat rectangular sheet of wood, although of course other rigid materials such as metals or synthetic resins may be substituted for wood. A large number of cylindrical bores 13 are drilled through the sheet 12, the axes of the bores 13 being arranged on a square lattice. The flat upper surface of the sheet 12 forms the support surface of the apparatus. For obvious practical reasons, this support surface is normally disposed horizontally when the apparatus is in use, and in the following description it will be assumed that the support surface is in a horizontal orientation, it being understood of course that the present invention is not restricted to any particular orientation of the components of the apparatus.

The apparatus 10 further comprises a stop member 14, which is substantially L-shaped. The stop member 14 is formed of metal and has two limbs 16 and 18 respectively. Both the limbs 16 and 18 are of rectangular cross-section, as best seen in FIG. 2. The undersurfaces of the limbs 16 and 18 lie in the same plane, so that the stop member 14 has a flat undersurface and can lie flat on the support surface of the sheet 12. Furthermore, the rectangular cross-sections of the limbs 16 and 18 provide first and second stop surfaces 20 and 22 respectively; when the stop member 14 lies flat upon the sheet 12, as shown in FIGS. 1 and 2, the stop surfaces 20 and 22 lie in vertical planes perpendicular to the upper surface of the sheet 12 and perpendicular to each other.

Three cylindrical projections 24, 26 and 28 are provided on the otherwise flat undersurface of the stop member 14, the axes of these cylindrical projections 24, 26 and 28 being perpendicular to the sheet 12. The projection 26 lies at the right angle of the stop member 14, while the projections 24 and 28 lie adjacent the free ends of the limbs 16 and 18 respectively. The projections 24, 26 and 28 on the stop member 14 can enter into, and fit snugly within, any three of the bores 13 in the sheet 12 (provided of course that the three bores 12 are chosen to have the correct spacings thereamong), thereby releasably securing the stop member 14 in a fixed position on the sheet 12. Since the projections 24, 26 and 28 can be inserted into any appropriately located three of the bores 13, the stop member 14 can be releasably secured to the sheet 12 in any one of a large number of different positions. To enable these positions to be identified, reference letters and numerals are placed along the edges of the sheet 12, letters A-L being placed along the left-hand edge (in FIG. 1) of the sheet 12 to identify rows of bores 13, while numbers are placed along the lower edge (in FIG. 1) of the sheet 12 to identify columns of bores 13. (First ease of illustration, only alternate reference numbers for the columns of bores are shown in FIG. 1.) To identify uniquely a specific position of the stop member 14, it is only necessary to specify the bore 13 in the sheet 12 into which the projection 26 in the stop member 14 should be placed, since the limb 16 should always extend parallel to the columns of bores 13 while the arm 18 should always extend parallel to the rows of bores 13. Thus, the position shown in FIG. 1 is denominated C-4 since the projection 26 enters the bore C-4. If adjustment of the position of the stop member 14 is required, the projections 24, 26 and 28 may be removed from the bores 13 and the stop member 14 translated parallel to the columns of bores 13 by a distance equal to the spacing between adjacent rows of the bores 13, and the projections 24, 26 and 28 reinserted through the bores 13, thereby fixing the stop member 14 in a new position, namely D-4. Alternatively, after removal of the projections 24, 26 and 28 from the bores 13, the stop member 14 may be slid parallel to the rows of bores 13 by a distance equal to the spacing between adjacent columns of the bores, and the projections 24, 26 and 28 reinserted into the bores 13, thereby placing the stop member 14 in position C-5. (Although, in the embodiment of the invention shown in FIGS. 1 and 2 the bores 13 are placed on a square lattice.so that the spacing between adjacent rows is equal to that between adjacent columns, one could alternatively arrange the bores 13 on a rectangular lattice in which the spacing between the rows is different from that between the columns.) It will readily be apparent that the stop member 14 can be placed in numerous other positions relative to the sheet 12, these positions being spaced from one other by various multiples of the spacing between adjacent rows and/or the spacing between adjacent columns of the bores 13.

The apparatus 10 shown in FIGS. 1 and 2 further comprises a base plate 32 disposed adjacent one edge of the sheet 12 but spaced therefrom. The base plate 32 can be moved manually relative to the sheet 12, but is formed of a heavy metal plate so that it will remain fixed relative to the sheet 12 while the apparatus is in use making a series of color measurements. A rod 34 extends vertically upwardly from the base plate 32, and a stage 36 is slidable along the rod 34. A locking lever 38 is mounted on the stage 36 and is movable between an unlocked position, in which the stage 36 can slide along the rod 34, and a locked position in which the stage 36 is releasably secured at a fixed position on the rod 34. An extension arm 40 extends from the stage 36 and radially outwardly from the rod 34. A metering means 42 in the form of a color-measuring instrument (such any of the commercially-available colorimeters discussed above) is mounted on the end the arm 40 remote from the rod 34 and lies above the sheet 12 and adjacent to the stop member 14.

In order to use the apparatus shown in FIGS. 1 and 2 to effect color measurements on a series of wrappers, carton blanks or similar objects, the stop member 14 is first releasably secured to the sheet 12 in any desired position by inserting the projections 24, 26 and 28 into the appropriate three bores 13 in the sheet 12. The lever 38 is then moved to its unlocked position and the stage 36 slid upwardly along the rod 34 until the instrument 42 is well spaced from the sheet 12. Next, an object 44, which has a pair of edges 46 and 48 at right angles to one another, is placed flat upon the sheet 12 and slid thereacross until the edges 46 and 48 abut the stop surfaces 20 and 22 respectively. The previous movement of the instrument 42 away from the sheet 12 allows the placement of the object 44 at the desired position on the sheet 12 to be effected without the instrument 42 obstructing the movement of the object 44, and without risk of damage to the instrument.

To carry out the actual color measurement, the locking lever 38 is again moved to its locked position, the stage 36 slid downwardly along the rod 34 until the instrument 42 lies very closely adjacent the object 44, and then the lever 38 is returned to its locked position. The instrument can now be used to effect measurement of the optical characteristics of the portion of the object 44 lying directly below the instrument 42; the portion of the object on which the measurements are effected is of course determined by the choice of the position at which the stop member 14 is releasably secured to the sheet 12.

After the necessary measurements have been effected, the locking lever 38 is shifted to its unlocked position, the stage 36 slid upwardly along the rod 34 and the lever 38 returned to its locked position. The object 44 may now be removed from the stop member 14, a similar object 44 substituted for the original object, and the lowering of the instrument 42 and the measurement of optical characteristics repeated. It should be noticed that because of the precise positioning of the objects 44 provided by the abutment of the edges 46 and 48 thereof against the stop surfaces 20 and 22 of the stop member 14, the same portion of each object 44 will lie beneath the instrument 42, and hence the optical characteristics will be measured on exactly the same portion of each similar object 44.

As will be apparent to those skilled in the art, the apparatus shown in FIGS. 1 and 2 is simple and inexpensive to construct, has no moving parts except for the stage 36 which slides along the rod 34 (and consequently the apparatus 10 requires virtually no maintenance) and is well-adapted for use by relatively unskilled personnel, as is necessary when the apparatus is to be used in conjunction with a packaging line.

The apparatus of the invention shown in FIGS. 1 and 2 may be modified by removing the projections 24, 26 and 28 from the stop member 14 and providing bores extending vertically through the stop member 14 at the same locations as the projections 24, 26 and 28, or at any other locations which will allow such bores through the stop member to overlie the bores 13 in the sheet 12. The releasable securing of the stop member 14 to the sheet 12 can then be effected by passing pegs through the bores in the stop member 14 and into appropriate ones of the bores 13 in the sheet 12. This modified apparatus of the invention using such pegs in place of the projections 24, 26 and 28 is hereinafter referred to as the peg apparatus of the invention.

The peg form of the invention allows for a further modification to enable the apparatus of the invention to be used for measurements on objects of varying shapes. In the specific embodiment of the invention shown in FIGS. 1 and 2, the stop member 14 is a single rigid integer with the limbs 16 and 18 at right angles to one another, and thus with the stop surfaces 20 and 22 also at right angles to one another. Thus, this specific embodiment of the apparatus of the invention can only be used with objects which have two edges at right angles to one another. To enable the peg apparatus to be used with objects (for example, blanks for tetrahedral packages) which have straight edges none of which are at right angles to one another, the peg apparatus may be modified by providing a pivot between the limbs 16 and 18 of the stop member 14 so that, by pivoting the limbs 16 and 18 relative to one another, the stop surfaces can be placed at varying angles to one another, thereby enabling a single stop member 14 to be used in color measurements on objects of varying shapes. If the apparatus is modified to allow the limbs 16 and 18 to pivot relative to one another, it is highly desirable that a locking means be provided to fix the angle between the limbs 16 and 18 while actual color measurements are taking place.

If the peg apparatus is thus modified to allow the limbs 16 and 18 to pivot relative to one another, it is of course necessary to make appropriate modifications to ensure that the bores in the stop member 14 overlie bores 13 in the sheet 12 so that the pegs can be inserted through both sets of bores to secure the stop member to the sheet 12. If the apparatus is only intended to allow for use with the limbs 16 and 18 at a limited number of angles relative to one another, it might be possible to arrange for appropriate correlation of the bores in the stop member and the sheet by providing multiple sets of bores in the stop member, one set for each of the useable angles between the limbs 16 and 18. (In theory, one might provide multiple sets of bores 13 in the sheet 12 and only one set of bores in the stop member 14, but the large number of bores 13 which would be required in each set and the likelihood that some of the bores would overlap one another will normally render the provision of multiple sets of bores 13 in the sheet 12 impracticable.) If, however, it is intended that the limbs 16 and 18 be used at a very large number of different angles to one another, or if the angle between the limb 16 and 18 must be made continuously variable, the provision of separate sets of bores in the stop member 14 becomes impracticable. In this case, one can provide only two bores in the stop member 14, so that only one limb of the stop member 14 is held in position directly by the pegs, and rely upon a locking mechanism to hold the other limb in the desired position. Alternatively, one might provide an arcuate slot in one limb, arrange for the peg to pass through this slot and provide means for clamping of the limb by means of the peg (for example, by making the bores in the sheet 12 threaded and using pegs in the form of threaded bolts which would engage the threads in the bores 13, thereby clamping the limb of the stop member beneath the head of the bolt). It will be appreciated that if only one of the limbs needs to be secured directly to the sheet 12 and the other is held in position by a locking mechanism, one could effect the securing of the stop member 14 to the sheet 12 by providing projections, as in the apparatus shown in FIGS. 1 and 2, on the one limb which is to be directly securred to the sheet 12.

Even if one uses a form of the apparatus of the present invention in which the angle between the limbs 16 and 18 of the stop member 14 is held constant, it may still be advantageous to allow the limbs 16 and 18 to lie at various angles to the lattice of bores 13. Such variation in the orientation of the limbs 16 and 18 allows for greater flexibility in selecting the area of the object disposed within the viewing area of the instrument 42. In this case, since only a limited number of angles of the limbs 16 and 18 to the rows and columns of bores 13 will normally be required, the necessary variation in the position of the limbs 16 and 18 can be achieved by providing a few sets of bores at various locations on the limbs 16 and 18, the locations of these additional sets of bores of course being chosen so the appropriate sets of bores are aligned exactly with the bores 13 in the sheet 12 when the limbs 16 and 18 are at the desired orientation with the respect to the lattice of bores 13.

Figure 3:
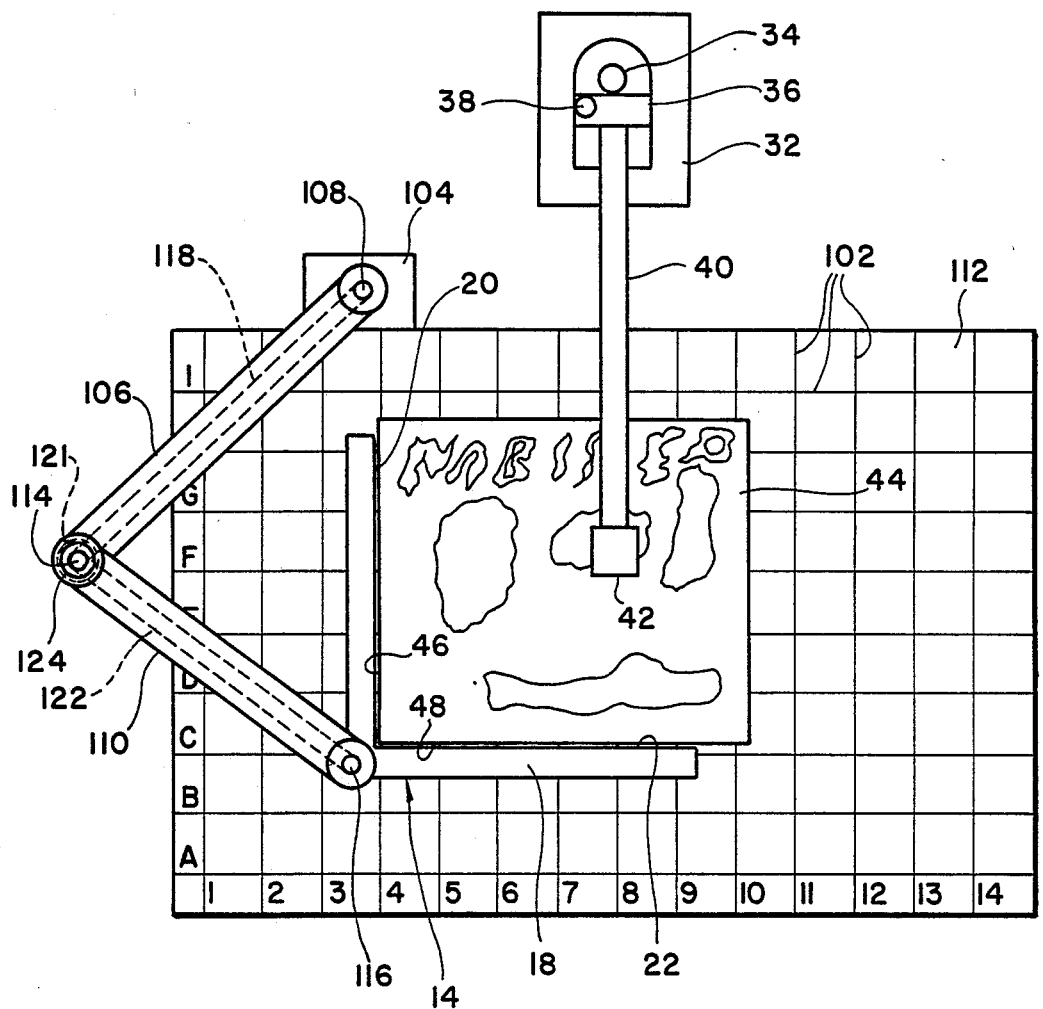
FIG. 3 is a top plan view of a second apparatus of the invention.

FIG. 3 is a top plan view of a second apparatus of the invention. This second apparatus has a support member 112 in the form of a flat sheet of wood having a flat upper surface which forms the support surface of the apparatus. However, in the second apparatus the sheet 112 is not provided with bores therein, but instead has a square grid of lines 115 marked thereon. The horizontal lines (in FIG. 3) are lettered, while the vertical lines are numbered, these letters and numbers being placed along two edges of the sheet 112 in the same manner as the letter and numeral markings of the rows and columns of bores 13 in FIG. 1.

A base plate 104 is fixedly secured to one edge of the sheet 112, and a first pivot arm 106 is mounted on the base plate 104 so as to pivot relative thereto about a vertical axis 108. A second pivot arm 110 is pivotally mounted on the first arm 106 for pivoting about an axis 114 disposed at the end of the arm 106 remote from the base plate 104. A stop member 14, identical to the stop member 14 shown in FIG. 1 except that it lacks the projections 24, 26 and 28 is pivotally mounted on the end of the second arm 110 remote from the first arm 106 and is provided with a locking knob 116 by means of which it can be locked relative to the arm 110 or rotated relative thereto.

The arms 106 and 110 are provided with a cord and pulley mechanism, schematically indicated at 118, 121 and 122, which operates in the same manner as similar mechanisms used in prior art drafting table arms and coordinates the pivoting of the first and second arms about their respective axes so that, when the stop member 14 is locked in position relative to the arm 110 by means of the locking knob 116, the stop member 14 can be moved in two dimensions across the support surface of the support member 112, while allowing the limbs 16 and 18 of the stop member 14 to retain the same orientation relative to the lines 102 on the upper surface of the sheet 112. An arm locking mechanism 124 is provided at the interconnection of the arms 106 and 110; this locking mechanism 124 has an unlocked position which permits the arms 106 and 110 to pivot freely about their respective axes, but can be placed in a locked position which prevents pivoting of the arms 106 and 110 about their respective axes.

The apparatus shown in FIG. 3 further comprises a lifting means comprising a base plate 32, a rod 34, a stage 36, a locking lever 38, an arm 40 and an instrument 42, all of which have exactly form and operate in exactly the same manner as the corresponding components in the first apparatus of the invention described above with reference to FIGS. 1 and 2.

The second apparatus of the invention shown in FIG. 3 is used in a manner closely similar to the first apparatus of the invention shown in FIGS. 1 and 2. To prepare the second apparatus for use, both locking mechanisms 116 and 124 are placed in their unlocked positions. The stop member 14 is then pivoted relative to the arm 110 until its stop surfaces 20 and 22 extend parallel to the vertical and horizontal (in FIG. 3) lines 102 respectively. The locking mechanism 116 is then placed in its locked position so that the stop surface 20 and 22 remain parallel to the lines 102. Next, the stop member 14 is slid across the upper surface of the sheet 112, with the arms 106 and 110 pivoting about their respective axes 108 and 114 respectively until the stop surface 20 is aligned with a desired one of the vertical lines 102 and the stop surface 22 is aligned with any desired one of the horizontal lines 102. The locking mechanism 124 is now moved to its locked position, thereby fixing the arms 106 and 110, and hence also the stop member 14 in position relative to the sheet 112. An object 44 is now placed with its edges 46 and 48 in contact with the stop surfaces 20 and 22 respectively, and the measurement of the desired optical characteristics effected in the same manner as described above with reference to the first apparatus of the invention shown in FIGS. 1 and 2.

In general, the first apparatus of the invention shown in FIGS. 1 and 2 is preferred to the second apparatus shown in FIG. 3 because manual alignment of the stop surfaces 20 and 22 with the lines 102 in FIG. 3 tends to be less accurate than the corresponding alignment achieved by placing pegs 30 through the bores 24, 26 and 28 shown in FIG. 1. Furthermore, despite the presence of the locking mechanisms 116 and 124 in the apparatus shown in FIG. 3, there is some risk of the stop member 14 "creeping" across the upper surface of the 112 in FIG. 3 when the second apparatus is used for a large number of successive measurements on similar objects, whereas such creeping is impossible with the projection-in-bore arrangement shown in FIG. 1. However, the second apparatus does have the advantage that the position of the stop member 14 can be varied continuously in two dimensions, whereas in the first apparatus the position of the stop member 14 can only be varied in increments equal to the spacing between adjacent bores 13. The continuous variability of the position of the stop member 14 in the second apparatus may be useful if it is necessary to use effect color determinations on designs having very small areas of certain colors.

I claim:

1. Apparatus for measuring an optical characteristic of a portion of an object having a first edge and a second edge not parallel to the first edge, the apparatus comprising:

a support member having a substantially flat support surface;

a stop member capable of lying adjacent the support surface and movable relative thereto along first and second non-parallel translation axes, the stop member comprising:

a first arm pivotally mounted for rotation about a pivot axis which is fixed relative to, and substantially perpendicular to, the support surface;

a second arm mounted on the first arm and pivotable relative thereto about a second arm axis spaced from, but substantially parallel to, the pivot axis;

a stop section secured to the second arm at a point spaced from the pivot arm axis, the stop section being provided with first and second stop surfaces which are not parallel to one another, the first and second stop surfaces being arranged on the stop section such that, when the stop section lies adjacent the support surface, the first and second stop surfaces both extend in one direction away from the plane of the support surface, thereby enabling the object to rest upon the support surface with its first and second edges in contact with the first and second stop surfaces respectively; and the stop member further comprising angular control means for controlling the pivoting of the first and second arms about their respective axes, such that as the first and second arms pivot about their respective axes, the first and second stop surfaces extend in fixed directions;

the apparatus further comprising locking means for releasably securing the stop member in any one of at least first, second and third positions relative to the support surface, movement from the first position to the second position requiring a translation along the first translation axis and movement from the first position to the third position requiring a translation along the second translation axis; and metering means for measuring the optical characteristic of the portion of the object overlying a predetermined point on the support surface.

2. An apparatus according to claim 1 wherein the first and second translation axes are substantially perpendicular to one another and the first and second stop surfaces lie substantially perpendicular to one another.

3. An apparatus according to claim 1 wherein the first and second stop surfaces are arranged on the stop member such that, when the stop member lies adjacent the support surface, the first and second stop surfaces extend substantially perpendicular to the plane of the support surface.

4. An apparatus according to claim 1 wherein the support surface is provided with markings to indicate the positions of the first and second stop surfaces along the first and second translation axes.

5. An apparatus according to claim 1 further comprising lifting means for moving the metering means between an operating position, in which the metering means lies adjacent the predetermined point on the support surface, and a non-operating position, in which the metering means lies at a greater distance from the predetermined point than in its operating position.

6. An apparatus according to claim 5 wherein the lifting means comprises:
　a lifting means support member extending substantially perpendicular to the support surface;
　a lifting means arm slideably mounted on the lifting means support member and carrying the metering means; and
　means for releasably securing the lifting means arm to the lifting means support member in the one operating position and at least one non-operating position.

7. An apparatus according to claim 1 wherein the locking means comprises means for locking the angular control means, thereby preventing pivoting of the first and second arms about their respective axes.

8. Apparatus for measuring an optical characteristic of a portion of an object having first and second edges substantially normal to one another, the apparatus comprising:
　a support member having a substantially flat support surface, the support surface having walls defining a plurality of recesses in the support surface, the recesses being disposed on a rectangular lattice;
　a stop member capable of lying adjacent the support surface and movable relative thereto along substantially orthogonal first and second axes, the stop member being provided with first and second stop surfaces extending substantially perpendicular to one another, the first and second stop surfaces being arranged on the stop member such that, when the stop member lies adjacent the support surface, the first and second stop surfaces both extend in one direction away from the stop surface and substantially perpendicular thereto, thereby enabling the object to rest upon the support surface with its first and second edges in contact with the first and second stop surfaces respectively, the stop member having a plurality of projections extending therefrom and capable of entering a plurality of the recesses in the support surface, thereby releasably securing the stop member in any one of at least first, second and third positions relative to the support surface, movement from the first position to the second position requiring a translation along the first axis and movement from the first position to the third position requiring a translation along the second axis;
　a lifting means support member extending substantially perpendicular to the support surface;
　a lifting means arm slideably mounted on the support member;
　means for releasably securing the lifting means arm to the lifting means support member in an operating position and at least one non-operating position; and
　a metering means for measuring the optical characteristic, the metering means being mounted on the lifting means arm such that, when the lifting means arm is in its operating position, the metering means lies adjacent a predetermined point on the support surface, thereby enabling the metering means to measure the optical characteristic of the portion of the object overlying the predetermined point on the support surface, and, when the lifting means arm is in a non-operating position, the metering means lies at a greater distance from the predetermined point than when the lifting means arm is in its operating position.

9. A process for measuring an optical characteristic of a portion of an object having a first edge and a second edge not parallel to the first edge, the process comprising:
　providing a support member having a substantially flat support surface;
　releasably securing, in a position fixed relative to the support surface, a stop member comprising:
　　a first arm pivotally mounted for rotation about a pivot axis which is fixed relative to, and substantially perpendicular to, the support surface;
　　a second arm mounted on the first arm and pivotable relative thereto about a second arm axis spaced from, but substantially parallel to, the pivot axis;
　　a stop section secured to the second arm at a point spaced from the pivot arm axis, the stop section being provided with first and second stop surfaces which are not parallel to one another, the first and second stop surfaces being arranged on the stop section such that, when the stop section is secured relative to the support surface, the first and second stop surfaces both extend in one direction away from the plane of the support surface, and
　　the stop member further comprising angular control means for controlling the pivoting of the first and second arms about their respective axes, such that as the first and second arms pivot about their respective axes, the first and second stop surfaces extend in fixed directions;
　the securing of the stop member relative to the support surface being effected by locking said angular control means, thereby preventing pivoting of the first and second arms about their respective axes,
　placing the object on the support surface with its first and second edges in contact with the first and second stop surfaces respectively;

placing a metering means for measuring the optical characteristic adjacent a predetermined point of the support surface; and measuring with the metering means the optical characteristic of the portion of the object overlying the predetermined point on the support surface.

10. A process according to claim 9 wherein the first and second edges of the object are disposed substantially perpendicular to one another and the first and second stop surfaces are disposed substantially perpendicular to one another.

11. A process according to claim 9 wherein, after the stop member has been releasably secured relative to the support surface, the first and second stop surfaces extend substantially perpendicular to the plane of the support surface.

12. A process according to claim 9 wherein the support surface is provided with markings to indicate the positions of the first and second stop surfaces along two non-parallel axes on the support surface.

13. A process according to claim 9 wherein the metering means is mounted upon a lifting means arm, the lifting means arm being itself slidably mounted on a lifting means support member extending substantially perpendicular to the support surface, and the placement of the metering means adjacent the predetermined point on the support surface is effected by sliding the lifting means arm along the lifting means support member, thereby moving the metering means from a non-operating position, in which the metering means is spaced from the support surface, to an operating position, in which the metering means lies closer to the support surface than in the non-operating position and adjacent the predetermined point on the support surface.

14. Apparatus for measuring an optical characteristic of a portion of an object having first edge and second edges not parallel to one another, the apparatus comprising:
 a support member having a substantially flat support surface, the support surface having walls defining a plurality of recesses in the support surface, the recesses being disposed on a rectangular lattice;
 a stop member capable of lying adjacent the support surface and movable relative thereto along substantially orthogonal first and second translation axes, the stop member being provided with first and second stop surfaces extending substantially perpendicular to one another, the first and second stop surfaces being arranged on the stop member such that, when the stop member lies adjacent the support surface, the first and second stop surfaces both extend in one direction away from the plane of the support surface and substantially perpendicular thereto, thereby enabling the object to rest upon the support surface with its first and second edges in contact with the first and second stop surfaces respectively, the stop member having a plurality of projections extending therefrom and capable of entering a plurality of the recesses in the support surface, thereby releasably securing the stop member in any one of at least first, second and third positions relative to the support surface, movement from the first position to the second position requiring a translation along the first translation axis and movement from the first position to the third position requiring a translation along the second translation axis; and
 metering means for measuring the optical characteristic of the portion of the object overlying a predetermined point on the support surface.

15. An apparatus according to claim 14 wherein the support surface is provided with markings to indicate the positions of the first and second stop surfaces along the first and second translation axes.

16. An apparatus according to claim 14 further comprising lifting means for moving the metering means between an operating position, in which the metering means lies adjacent the predetermined point on the support surface, and a non-operating position, in which the metering means lies at a greater distance from the predetermined point than in its operating position.

17. An apparatus according to claim 16 wherein the lifting means comprises:
 a lifting means support member extending substantially perpendicular to the support surface;
 a lifting means arm slideably mounted on the lifting means support member and carrying the metering means; and
 means for releasably securing the lifting means arm to the lifting means support member in the onber operating position and at least one non-operating position.

* * * * *